United States Patent [19]

Linnecke et al.

[11] Patent Number: 4,748,042
[45] Date of Patent: May 31, 1988

[54] METHOD AND APPARATUS FOR IMPRINTING MEMBRANES WITH PATTERNS OF ANTIBODY

[75] Inventors: Carl Linnecke, Arcadia; Ailene Herranen, Woodland Hills; Alan S. Fraser, Whittier, all of Calif.

[73] Assignee: V-Tech, Inc., Pomona, Calif.

[21] Appl. No.: 32,460

[22] Filed: Mar. 31, 1987

[51] Int. Cl.⁴ .................. A01N 1/02; G01N 31/22; G01N 33/543; G01N 33/544
[52] U.S. Cl. ........................................ 427/2; 422/56; 422/57; 436/518; 436/530; 436/531; 436/818
[58] Field of Search .................. 427/2; 436/518, 530, 436/531; 436/818; 422/56, 57

[56] References Cited

U.S. PATENT DOCUMENTS 4,216,245  8/1980  Johnson ........................... 427/2

Primary Examiner—Michael R. Lusignan
Attorney, Agent, or Firm—Drucker & Sommers

[57] ABSTRACT

A method and apparatus that imprints protein binding membranes with predetermined patterns, determined by (a) a pattern cut in a porous foam, or (b) a circular pattern achieved by contacting a drop of protein containing solution. The apparatus and process are particularly well adapted to forming the active surface for devices that detect antigens with antibodies.

22 Claims, 2 Drawing Sheets

METHOD AND APPARATUS FOR IMPRINTING MEMBRANES WITH PATTERNS OF ANTIBODY

BACKGROUND OF THE INVENTION

1. Field of the Invention

This invention relates to apparatus for printing, and particularly apparatus for printing patterned designs containing antibody.

2. Prior Art

It is known that proteins bind strongly to certain membranes. In particular, antibodies are a class of proteins known to bind to protein binding membranes. Such membranes include nitrocellulose and activated nylon membranes. The membranes, at the time of impregnation, will bind to nearly any protein. It is essential that only the proper antibodies contact the binding membrane.

One method preparing an antibody diagnostic or analytical kit involves the impregnation of the membrane with two antibodies, one that is reactive for the antigen being tested for, and the other that is reactive the reagents used in the test. In this way, the reagents and lab technique are always verified for each test. A test that is negative because of the absence of the anitgen can be differentiated from a false negative due to poor reagents or improperly applied reagents. A two-antibody-type test requires that the membranes be carefully impregnated with both antibodies.

Applicant knows of no apparatus or system that allows for impregnation of protein binding membranes. Applicant's apparatus and system therefore represent an advance in the art of creating easily usable antibody test kits.

SUMMARY OF THE INVENTION

An aspect of this invention is an apparatus for placing antibodies in a predetermined pattern on a membrane that binds for antibodies comprising means for forming a first transferable pattern of a first antibody solution; a protein binding membrane; and means for presenting the membrane to the means for forming a transferable pattern of a first antibody solution.

Another aspect of this invention is a method for impregnating a protein binding membrane with a predetermined pattern of antibody comprising forming a transferable pattern of a first antibody solution; presenting a protein binding membrane to the formed pattern of antibody solution; and removing said membrane from contact with said pattern.

DETAILED DESCRIPTION OF THE PREFERRED EMBODIMENT

Figure 1:
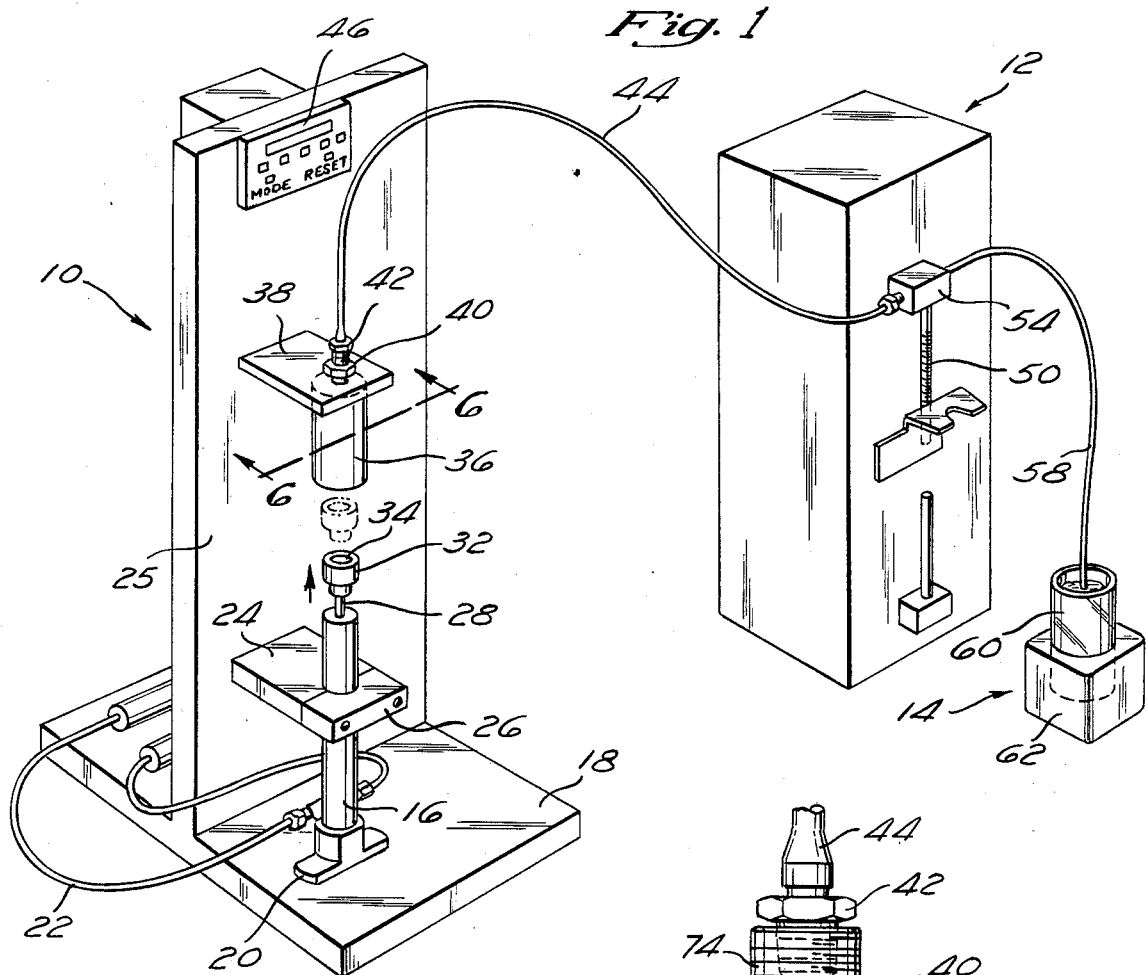
FIG. 1 shows a perspective view of an embodiment of this invention.

Referring the FIG. 1, the membrane printer 10 is connected to fluid pump means 12 by a tube 44. The fluid pump means is connected to a fluid reservoir 14 by fluid reservoir supply tube 58 containing the antibody solution. The membrane printer has an air piston 16 attached to a base support plate 18 by a piston base support 20. Pressurized air for the air piston is supplied to the air pressure line 22. The piston is further supported by the air piston support collar 24. The air piston support collar has a removable collar member 26 that allows the air piston to be easily removed. The piston support collar is attached to a vertical support plate 25 that is attached to the base support plate.

A piston extension rod 28 extends from the air piston housing and terminates in a cap support piece. A cap 32 having an aperture in its top, for an immunological testing system, is snuggly supported by the cap support piece. The membrane 34 is centered in the aperture. The cap is raised and the membrane is presented to the membrane impregnator 36 when the air piston is actuated, as shown in phantom.

The membrane impregnator is supported on a membrane impregnator support collar 38 by a membrane impregnator retaining screw 40. The membrane impregnator support collar is attached to the vertical support plate. The membrane impregnator has a tube receiving nut, which receives a tube from the fluid pump means. The tube receiving nut is hollow and allows the passage of fluid. The membrane printer and the fluid pump means are controlled by a printer and pump control 46. The tube is connected to a pump means tube receiving nut 48.

At its other end, the tube 44 is connected to a pump flow valve 54, which controls the flow from the fluid reservoir to a volumetric measuring means 50 out to the membrane printer 10. The volumetric measuring means measures out a precise amount of fluid and injects it into the tube. The preferred volumetric measuring means is a microsyringe that can measure microliter amounts accurately. The plunger on such a syringe is attached to the volumetric measuring means activation piston, which automatically moves the plunger down, to draw fluid from the fluid reservoir, and then up again, to force the fluid to the membrane printer.

The pump flow valve 54 has two one-way valves. The first one-way valve prevents the flow of fluid from the membrane printer to the fluid pump means when the volumetric measuring means is acquiring fluid. The second one-way valve prevents the volumetric measuring means from injecting the fluid back into the fluid reservoir.

The pump flow valve is connected to the fluid container 60 by a fluid reservoir supply tube. The container can be any container that conveniently holds a volume of fluid. One particularly convenient container when dealing with small amounts of fluid is a test tube. If a test tube is used, a container support 62 must also be used.

The fluid within the container will contain the antibody that is to be imprinted on the protein binding membrane. Depending on the maufacturing technique used, it may be desirable to have a dye in the fluid so that the assembly work force can tell by inspection whether the membrane has been impregnated with the fluid.

Figure 2:
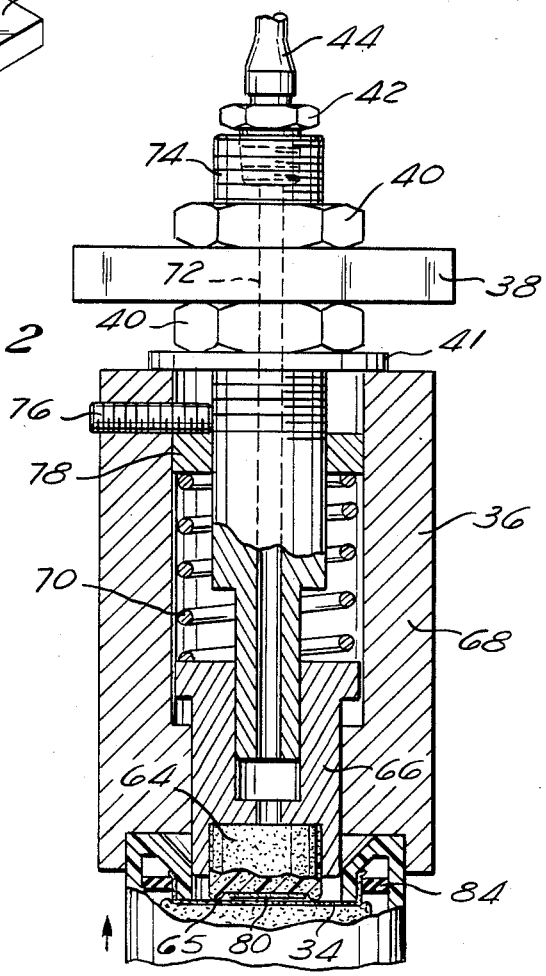
FIG. 2 shows a cut-away portion of the membrane impregnator of this invention.

Referring now to FIG. 2, the impregnator 36 is supported on the membrane impregnator support collar 38 by a pair of retaining screws 40. The retaining screws engaged external threads on the fluid transport member 74. The fluid arrives from the tube 44 to the tube receiving nut 42. The fluid flows through the fluid channel 72 to the porous membrane contact head 64.

The contact head 64 is preferably made out of a porous foam material. The fluid will impregnate it by capillary action and flow through to the surface facing the membrane 34. The membrane is retained within the cap 32 by retaining ring 84.

The cap and the membrane are urged upwardly into contact with the contact head by the cap support piece 30. The membrane contact head is supported by a membrane contact head support 66, which is mounted within the membrane impregnator body 68 such that it can travel in a longitudinal direction within the body. Therefore, the membrane contacts the contact head, moving the contact head upwardly a predetermined distance. At the top of the stroke the membrane contacts the contact head with a predetermined amount of pressure. This pressure is enough to transfer the antibody solution to the contacted surface of the membrane.

The return spring 70 urges the membrane contact head support back into its original position after each contact with a membrane. The predetermined pressure can be altered by adjusting the body position on the fluid transport member by use of an adjustment ring 41. By moving the body member downwardly the spring is compressed more against the return spring retainer and the contact head support member.

The membrane is critical to the assembly of a usable testing apparatus. The membranes that are used bind proteins tenaciously. Therefore, all proteins but the correct antibody must be kept from contact with the membrane. Furthermore, the membranes are relatively delicate. The pressure exerted by the contact head must not exceed that required to impregnate the upper surface of the membrane. The operator of the finished diagnostic device can only see the top surface, so excess antibody that penetrates the interior volume of the membrane is wasted.

Figure 3:
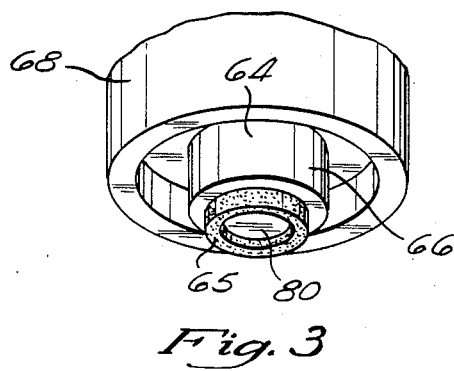
FIG. 3 shows a perspective view of the impregnator of this invention.

Referring to FIG. 3, the contact head 64 has an annular pattern 65 cut or etched into its bottom contact surface. To prevent extraneous material from contacting the membrane the pattern is protected with a design mask 80. The design mask can be a small piece of plastic having the appropriate shape attached to the membrane contact head. The membrane contact head is supported within the membrane contact head support 66, which, in turn, is disposed within the body member 68.

In the use of this invention the fluid contact head is kept moist with fluid by the action of the fluid pump means. The amount of fluid to be pumped onto the head is determined emperically, that is one observes the quality of the markings on each membrane during a series of membranes. When the quality has deteriorated to a predetermined level of poor quality the fluid pump means should inject new fluid into the head.

The digital control means 46 allows the contact head to be kept moist. One can then keep the head moist enough to give good quality markings on the membrane, but not so moist as to accidentally run liquid onto the membrane. The digital control means are well known in the art.

During the operation of imprinting the membrane with antibody, the cap 32 is placed onto the cap support piece 30. The cap can be placed onto the support piece by manual manipulation of an operator, or it can be placed automatically by a robot arm means. Once the cap is securely in place, the air piston is actuated raising the cap toward the membrane impregnator 36. The membrane engages the membrane contact head forcing it, and the membrane contact head support 66, upwardly into the impregnator body. At the top of the piston's cycle, the membrane contact head thereby provides the membrane with a predetermined amount of pressure.

A precut design or pattern can be cut or etched onto the membrane resulting of downward onto the membrane resulting in downward of extensions 64 in the membrane contact head. The areas of the membrane contact head that correspond to the areas of the pattern where no fluid is to be printed are protected by the design mask 80. In the case shown, where the design is a ring, the design mask is a circular piece of this plastic secured, by, for example, gluing to the center of the contact head.

After the cap has contacted the membrane impregnator, the air piston lowers the cap where it can be removed by manipulation or robot arm means from the cap support. If the fluid has a dye, particularly a dye that is more visible when wet than dry, an assembly operator can inspect each cap as it comes out of the above-described operation to make sure that the complete design, and only the complete design, has been properly transferred to the membrane.

After several caps have been impregnated, the volumetric measuring means provides a new amount of fresh fluid to the membrane impregnator. Typically, two or three caps can be impregnated and then the membrane impregnator is activated sending 3 to 6 microliters of fluid into the tube 44.

Figure 4:
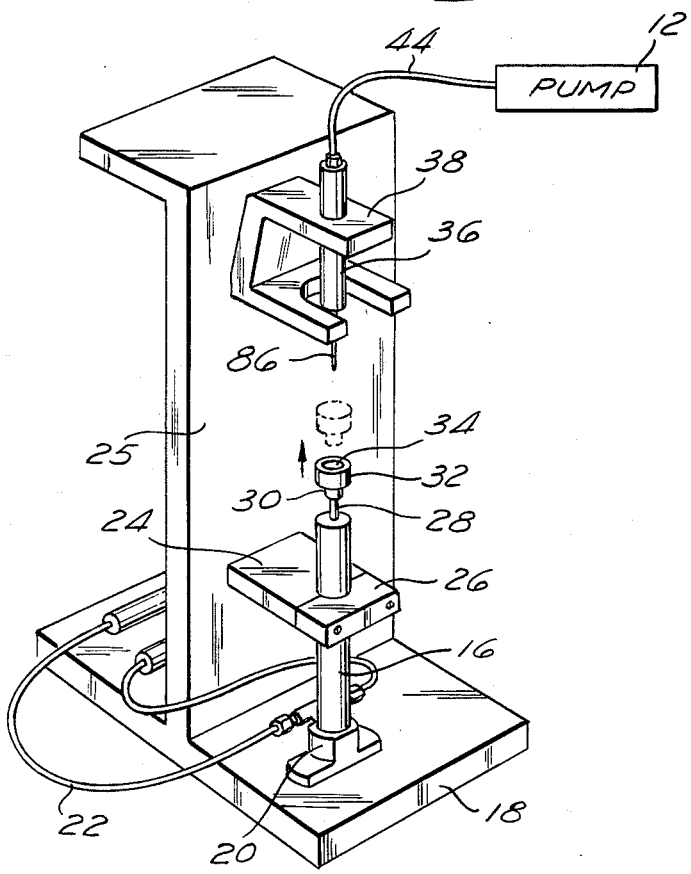
FIG. 4 shows a perspective view of an alternate embodiment of this invention.

Turning now to FIG. 4, an alternate embodiment is shown with the desired pattern is a centered dot. A piston base support 20 is attached to a base member 18, which holds an air piston 16 oriented so the piston operates in a substantially vertical axis. The air pressure line 22 supplies the air pressure required to actuate the air piston. The air piston is supported by a piston support collar 24, which has a removable collar member 26 to aid in removal of the air piston for maintenance. The air piston support collar is attached to a vertical support plate 25. The air piston has a piston extension rod extending from the top of the air piston 28 terminating in a cap support piece 30. The cap 32 having a central aperture is secured on the cap support piece. The membrane 34 that is to be impregnated is on the top center area of the cap.

The membrane is presented to a drop (not shown) that is formed at the end of a tubular drop former 86. The membrane contacts only the drop and not the tubular drop former. The drop is adsorbed onto the surface of the membrane by capillary action.

The membrane impregnator 36 is held on to the vertical support plate by a membrane impregnator support collar 38. A tube 44 leads to a fluid pump means 12 shown schematically in the drawing. The fluid pump means operates as heretofore described with the one exception that the volumetric measuring means is operated each time a cap is to be impregnated. The volumetric measuring means measures out the volume of each drop that is to be formed on the tubular drop former.

Of course, one could use a cut pattern on a foam member, as shown in FIGS. 2 and 3 to create a centered dot. The foam would extend downwardly in the center and be protected by a ring shaped design mask.

Figure 5:
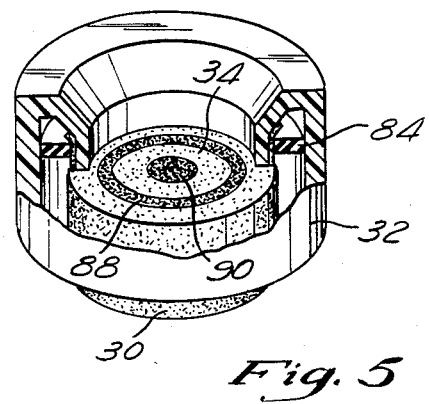
FIG. 5 shows a partial cut-away perspective drawing of a cap having a membrane that has been impregnated with a pattern of antibody.

Referring now to FIG. 5, the piston extension rod 28 terminates in the cap support piece 30. The cap 32 is secured on the cap support piece. The membrane 34 is disposed within the cap and rests on the cap support piece. It is retained in the cap by the retaining ring 84.

The membrane is shown with a design imprinted on it. The ring 88 is imprinted by the membrane impregnator as shown in FIG. 2. The dot 90 is impregnated by the membrane impregnator as shown in FIG. 4. In a preferred embodiment of this invention the ring will contain one antibody, and the dot will contain another. Preferably, the dot will contain the antibody that is reactive with the antigen that is being tested for. For example, in a pregnancy test, the dot will contain anti-hCG. The human female produces hCG during the early stages of pregnancy, and reaction of a bodily fluid confirming the existence of hCG confirms pregnancy. The ring can contain an antibody that is reactive with the reagents used in the test, for example, anti-horseradish peroxiodase.

As noted before, the membrane will bind proteins tenaciously. After the pattern of antibodies has been placed on the membrane, the unexposed surface must be neutralized. A preferred method is to drain a protein containing solution through the impregnated membrane. A preferred protein for the hCG test is casein. Then the protein binding ability of the membrane will be saturated. Of course, the protein selected for saturation purposes must not cross react with either the antibodies impregnated on the membrane, or with the antigen. So it is possible that some other protein other than casein might be required for certain combinations of testing antibodies and antigens.

An antigen test kit, made with a cap impregnated by the present invention, is used by contacting the membrane with a fluid suspected to contain the antigen. The fluid is placed in the well 92, and drawn through the membrane. If the antigen is present, it binds to the antibodies bound to the membrane, which are the antibodies placed there by the membrane impregnator. A second, labelled antibody is then passed through the membrane. Any antigen present will therefore be bound to the membrane on one end, and bound to a labeled antibody on the other, forming a kind of "sandwich." Detection of the label is equivalent to detecting the antigen.

One of the reagents will contain a known amount of the antigen that reacts with the antibody in the ring, in this example horseradish peroxiodase. The reagent containing labeled antibody will contain antibodies that are reactive with the antigen being tested for and horseradish peroxidase.

The reagents and the technique of the laboratory technican can be double checked with the double antibody system. The ring 88 should always show a positive test, but the dot 90 may or may not show positive. If the ring does not show a positive test then the test results are invalid, and the test should be repeated. This way spurious false negative results are reduced.

Figure 6:
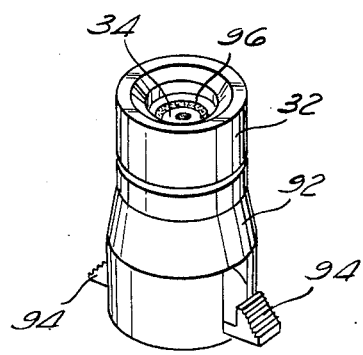
FIG. 6 shows a perspective view of an assembled immuno tester having a membrane made by use of this invention.

Referring now to FIG. 6 a body member 92 is mated to the cap 32. Preferably the cap and the body are made of resilient plastic and snap fitted. The handles 94 are attached to a piston disposed within the body member. Movement of the piston downwardly creates a region of reduced air pressure. A volume of the fluid to be tested is placed in the depression for receiving fluid 96. The region of reduced air pressure causes the fluid to flow past the membrane 34 having a pattern of antibody impregnated thereon. For a more complete description see my copending U.S. patent application Ser. No. 07/006874.

Although specific embodiments have been described, the scope of the invention should be considered limited only by the appended claims.

We claim:

1. An apparatus for placing antibodies in a predetermined pattern on a membrane that binds for antibodies comprising:
   means for forming a first transferable pattern of a first antibody solution;
   a protein binding membrane; and
   means for presenting the membrane to the means for forming a transferable pattern of a first antibody solution.

2. The apparatus of claim 1, wherein said means for forming a transferable pattern of fluid has a predetermined design.

3. The apparatus of claim 2, wherein the predetermined design is formed on a shaped foam member.

4. The apparatus of claim 3, wherein said shaped foam member engages the membrane with a predetermined pressure.

5. The apparatus of claim 2, wherein said design is formed by a tubular drop former.

6. The apparatus of claim 1, wherein said membrane is disposed within a cap.

7. The apparatus of claim 6, wherein said membrane is secured within said cap by a retaining ring.

8. The apparatus of claim 1, including a fluid pump means that replenishes the first antibody solution supply to the means for forming a transferable pattern of the first antibody solution after a predetermined number of applications.

9. The apparatus of claim 1, including a separate means for forming a second transferable pattern of a second antibody solution wherein said second tranferable pattern is distinctly different from said first pattern.

10. A method for impregnating a protein binding membrane with a predetermined pattern of antibody comprising:
    forming a transferable pattern of a first antibody solution;
    presenting a protein binding membrane to the formed pattern of antibody solution; and
    removing said membrane from contact with said pattern.

11. The method of claim 10, including the steps of:
    forming a second transferable pattern of a second antibody solution;
    contacting the membrane with said second transferable pattern; and
    removing the membrane from said second transferable pattern, thereby providing a membrane having two distinct patterns of two different antibodies impregnated thereon.

12. The method of claim 11, including the step of saturating the protein binding sites on the membrane.

13. The method of claim 12 including the step of draining a solution containing a protein not reactive to the antibody or antigen through the membrane.

14. The method of claim 10 wherein said first antibody solution contains anti-hCG.

15. The method of claim 11 wherein said first antibody solution contains anti-hCG and said second antibody solution contains anti-horseradish peroxidase.

16. The method of claim 13 wherein said protein not reactive to the antibody or antigen is casein.

* * * * *